United States Patent [19]

Hall et al.

[11] 3,931,306

[45] Jan. 6, 1976

[54] PROCESS FOR PRODUCING ISOMER MIXTURES CONTAINING HIGH PROPORTIONS OF CIS-2-METHYL-3-PENTENOIC ACID

[75] Inventors: John B. Hall, Rumson; Manfred Hugo Vock, Locust; Joaquin Vinals, Red Bank, all of N.J.; Edward J. Shuster, Brooklyn, N.Y.

[73] Assignee: International Flavors & Fragrances Inc., New York, N.Y.

[22] Filed: July 22, 1974

[21] Appl. No.: 490,717

Related U.S. Application Data

[63] Continuation-in-part of Ser. No. 408,854, Oct. 23, 1973, abandoned.

[52] U.S. Cl............... 260/526 N; 131/17; 131/144; 252/89; 252/132; 252/522; 426/534
[51] Int. Cl.$^2$.......................................... C07C 57/02
[58] Field of Search............................. 260/526 N

[56] References Cited
OTHER PUBLICATIONS
McGreer et al., Can. J. Chem., 41, 726–731 (1963).

Primary Examiner—Lorraine A. Weinberger
Assistant Examiner—Jane S. Myers
Attorney, Agent, or Firm—Arthur L. Liberman, Esq.; Harold Haidt, Esq.

[57] ABSTRACT

A method for producing mixtures containing greater than 50% cis 2-methyl-3-pentenoic acid comprising first reacting methyl acetylene with a methyl magnesium halide to form a methylacetylene magnesium halide Grignard reagent; then reacting the methyl acetylene magnesium halide Grignard reagent with acetaldehyde to form a 3-pentyn-2-ol magnesium halide salt; then hydrolyzing the magnesium halide salt to form 3-pentyn-2-ol; then halogenating the 3-pentyn-2-ol to form a 4-halo-2-pentyne; then reacting magnesium with the 4-halo-2-pentyne to produce a 4-magnesium halo-2-pentyne Grignard reagent; then reacting the 4-magnesium halo-2-pentyne Grignard reagent with carbon dioxide to form a magnesium halo-carboxylate salt mixture of compounds having the structures:

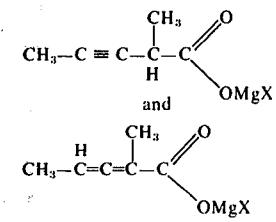

and (wherein X is halogen); then hydrolyzing the magnesium halo-carboxylate salt mixture to form a mixture of carboxylic acids having the structures:

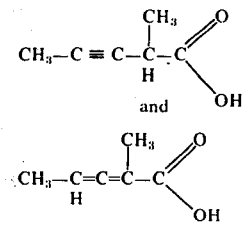

and then hydrogenating the aforementioned mixture of carboxylic acids to form a mixture containing 80% cis-2-methyl-3-pentenoic acid and 20% of 2-methyl-2-pentenoic acid.

1 Claim, No Drawings

PROCESS FOR PRODUCING ISOMER MIXTURES CONTAINING HIGH PROPORTIONS OF CIS-2-METHYL-3-PENTENOIC ACID

This application is a continuation-in-part of application for U.S. Letters Pat. Ser. No. 408,854 filed on Oct. 23, 1973 now abandoned.

BACKGROUND OF THE INVENTION

The present invention relates to isomeric mixtures containing greater than 50% cis-2-methyl-3-pentenoic acid produced by, interalia, a novel process and novel compositions using such mixtures of cis and trans isomers of 2-methyl-3-pentenoic acid to alter the flavor and/or aroma of consumable materials.

There has been considerable work performed related to substances which can be used to impart (or enhance) flavors to (or in) various consumable materials. These substances are used to diminish the use of natural materials, some of which may be in short supply and to provide more uniform properties in the finished product. Sweet, fruity, strawberry, winey-cognac, butter-like, rum-like, and butterscotch aromas as well as sweet, strawberry, nutty-coconut, fatty, butter-like, rum-like and butterscotch-like tastes are particularly desirable for many uses in foodstuff flavors. Green, sweet, sharp strawberry notes are desirable in perfume compositions. Notes having turkish-like characteristics as well as aromatic, sweet, bitter, woody and smokey notes are desirable in tobacco flavoring compositions.

U.S. Pat. No. 3,499,769 issued on Mar. 10, 1970 discloses processes for imparting a fresh fruity flavor (particularly strawberry flavor) to foods by adding a small amount of 2-methyl-2-pentenoic acid to the foodstuff. In U.S. Pat. No. 3,499,769 it is emphasized that the basic nuance imparted by 2-methyl-2-pentenoic acid is a "berry" flavor. Quite unexpectedly, the novel isomeric mixture of the instant invention has properties different in kind from the 2-methyl-2-pentenoic acid of U.S. Pat. No. 3,499,769 which is only fruity and strawberry-like and does not have the sweet, fruity, butter-like, rum-like and butterscotch aroma and taste qualities of the isomeric mixture of the instant invention. Other isomeric mixtures of 2-methyl-3-pentenoic acid are shown to be prepared by Boorman and Linstead, J.Chem.Soc. 1935, 258–67 (abstracted by Chem. Abstracts, Vol. 29, pages 2912 (7/8). 2-Ethyl-3-pentenoic acid is shown to be prepared by Fichter and Obladen, Berichte, 42, 4703-7 by distillation of alpha-ethyl gamma methyl paraconic acid which, in turn, is formed by reduction using a sodium-mercury amalgam of ethyl-alpha-ethyl aceto-succinate. The above-disclosed processes produce isomer mixtures which are considered to be different in kind insofar as their organoleptic properties are concerned from the isomer mixtures produced by the process of the instant invention.

Ethyl-2-methyl-3-pentenoate (95% 3:1 trans:cis isomer and 5% ethyl-2-methyl-2-pentenoate) has been offered as a development chemical by Toray Industries, Inc. of 2, Nihonbashi-Muromachi 2-chome, Chuo-Ku, Tokyo, Japan.

McGreer, et al, Can. J. Chem., 41, 726,31 (1963) discloses the production of various alkyl esters of pentenoic and butenoic acids by means of pyrolysis of 3,5-dimethyl-3-carbomethoxy $\Delta^1$-pyrazoline. Thus, on page 728 of the McGreer article, products having the following structures are shown to be produced:

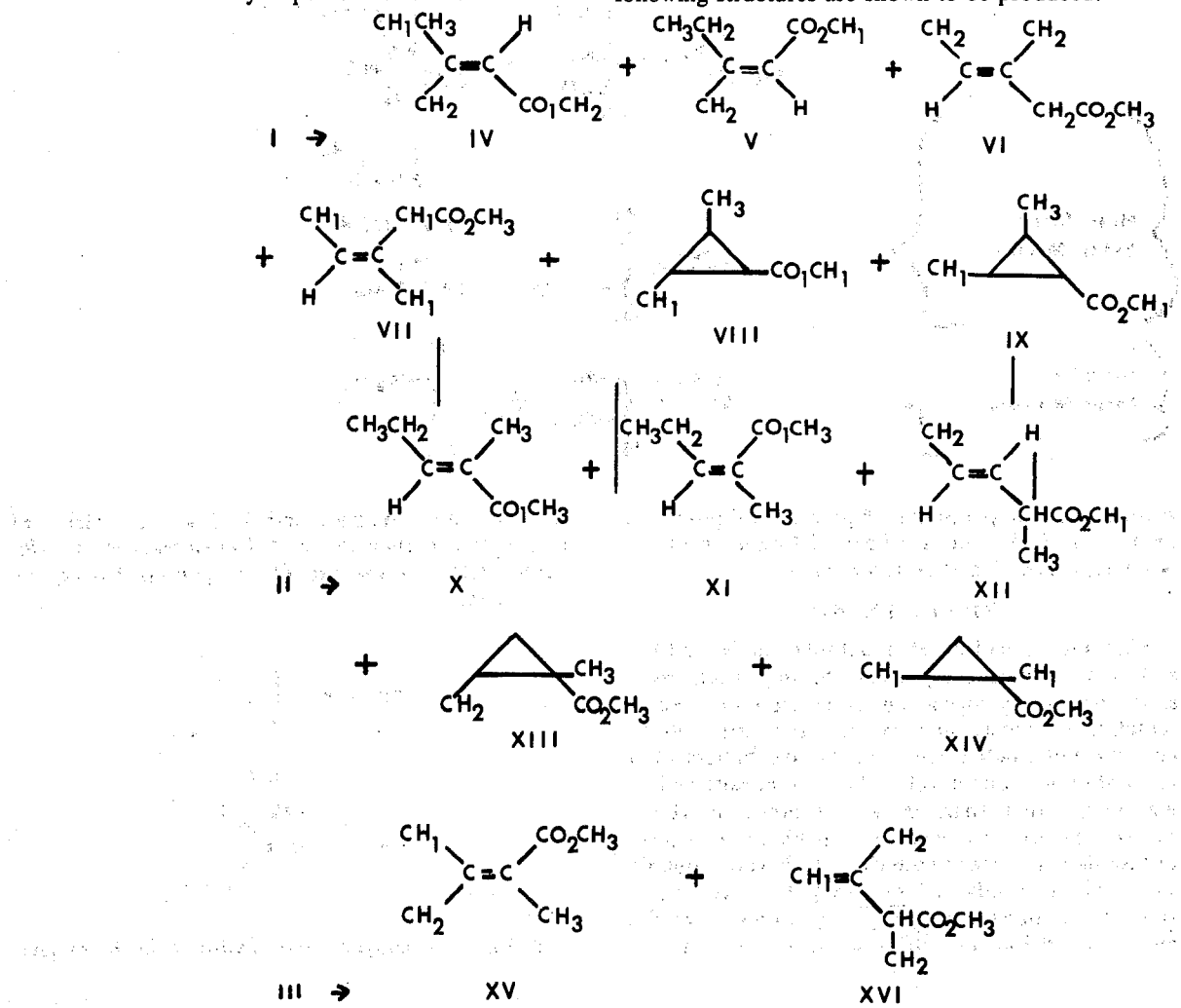

+ 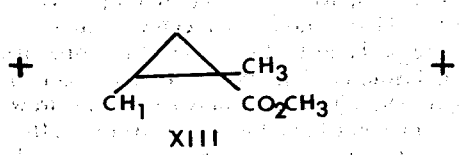 + 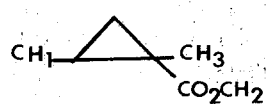

XIII                 XIV

Tsuji, et al, J.Am.Chem.Soc., 86, (20) 4350–3 (1964) discloses the production of alkyl alkenoates by means of reaction of carbon monoxide, alkenyl halides and alkanols with use of palladium chloride as a catalyst. Other methods for the synthesis of alkyl alkenoates are set forth in the following references:

i. French Pat. No. 1,389,856, issued Feb. 19, 1965;
ii. Brewis and Hughes, Chem. Communications, (8), 157–8 (1965);
iii. Bordenca and Marsico, Tetrahedron Letters (16), 1541–3 (1967); and
iv. Hosaka and Tsuji, Tetrahedron, 27, (16) 3821–9 (1971).

None of the above references sets forth a process for preparing the cis isomer of an alkyl pentenoic acid or mixtures containing more than 50% cis isomer.

Felkin, et al., Ann.Chem. (Paris) 6 (1), 17–26 (1971) discloses processes for producing "high cis" and "high trans" 2-methyl-3-pentenoic acid and methyl-2-methyl-3-pentenoate mixtures, according to the following reaction sequences:

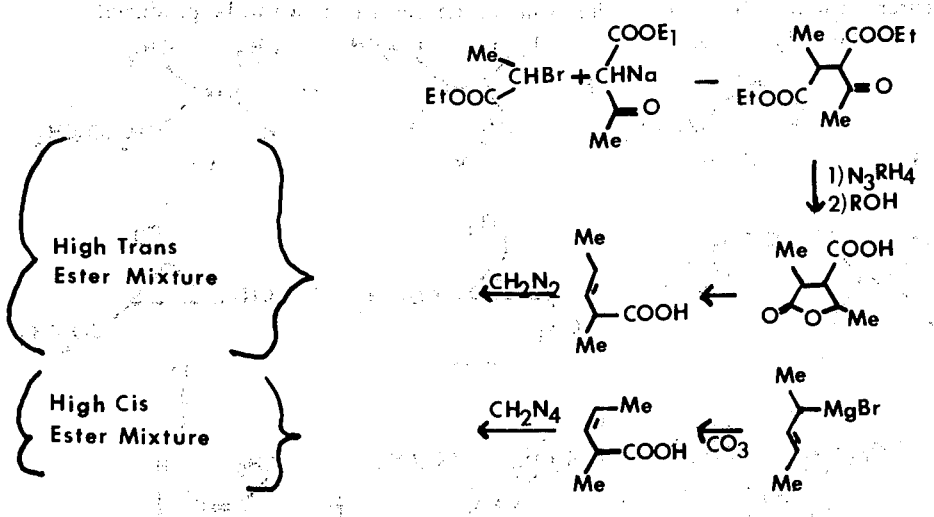

A process for preparing the "high cis" acid mixture is set forth in Felkin, et al, Chemical Communications, No. 802, pages 75 and 76 (Dec. 29, 1965).

THE INVENTION

It has now been discovered that solid and liquid foodstuff and flavoring compositions having sweet, fruity, strawberry, winey-cognac, butter-like, rum-like, butterscotch-like aromas and sweet, strawberry, nutty-coconut, fatty, butter-like, rum-like and butterscotch-like taste notes; and novel perfume compositions having green, sweet, sharp strawberry notes; as well as tobacco flavoring compositions capable of imparting a turkish-like character to tobacco and having aromatic, sweet, bitter, woody and smokey notes may be provided by the utilization of isomer mixtures containing more than 50% cis-2-methyl-3-pentenoic acid (hereinafter termed "high cis-2-methyl-3-pentenoic acid" produced either (i) according to a process involving the steps of first preparing a 2-halo-3-pentene; then admixing said 2-halo-3-pentene with magnesium to form a 2-magnesium halo-3-pentene; then reacting said 2-magnesium halo-3-pentene with carbon dioxide to form a magnesium halo salt of 2-methyl-3-pentenoic acid and finally hydrolyzing the said salt in the presence of acid to form a novel isomer mixture containing a ratio of 60% cis-2-methyl-3-pentenoic acid and 40% trans-2-methyl-3-pentenoic acid or (ii) according to a process involving first reacting methyl acetylene with a methyl magnesium halide to form a methylacetylene magnesium halide Grignard reagent; then reacting the methyl acetylene magnesium halide Grignard reagent with acetaldehyde to form a 3-pentyn-2-ol magnesium halide salt; then hydrolyzing the magnesium halide salt to form 3-pentyne-2-ol; then halogenating the 3-pentyne-2-ol to form a 4-halo-2-pentyne; then reacting magnesium with the 4-halo-2-pentyne to produce a 4-magnesium halo-2-pentyne Grignard reagent; then reacting the 4-magnesium-halo-2-pentyne Grignard reagent with carbon dioxide to form a magnesium halo-carboxylate salt mixture of compounds having the structures:

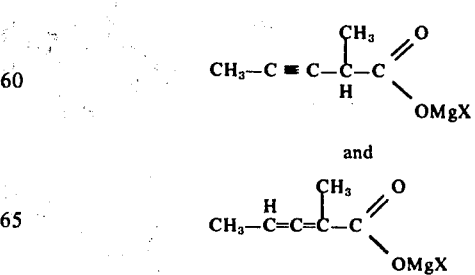

(wherein X is halogen); then hydrolyzing the magnesium halo-carboxylate salt mixture to form a mixture of carboxylic acids having the structures:

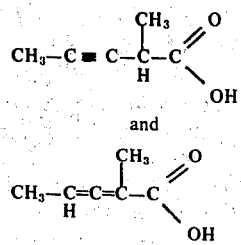

and then hydrogenating the aforementioned mixture of carboxylic acids to form a mixture containing 80% cis-2-methyl-3-pentenoic acid and 20% 2-methyl-2-pentenoic acid.

The "high cis" 2-methyl-3-pentenoic acid of our invention is intended to include singly and in admixture the two stereoisomers of 2-methyl-3-pentenoic acid having the structures:

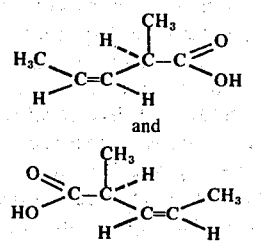

Thus, the "high cis" 2-methyl-3-pentenoic acid of our invention is capable of supplying and/or potentiating certain flavor and aroma notes usually lacking in many fruit flavors as well as turkish tobacco flavors heretofore provided. Furthermore, the 2-methyl-3-pentenoic acid isomer mixture of our invention is capable of supplying certain fragrance notes usually lacking in many perfumery materials, for example, strawberry fragrances.

One process, set forth in the prior art, for producing a high cis 2-methyl-3-pentenoic acid isomer mixture involves the steps of:
  a. First preparing a 2-halo-3-pentene by intimately admixing hydrogen bromide with 1,3-pentadiene at a temperature of from −20° up to +30°C, preferably, from 0° up to 10°C and at a pressure, preferably, of atmospheric pressure. The 1,3-pentadiene (otherwise known as "piperylene" preferably has a purity of 90% but 50% piperylene may also be used. The 2-halo-3-pentene thus produced may be used in its crude form without further purification in subsequent reactions;
  b. The 2-halo-3-pentene is then reacted with magnesium to form a Grignard reagent, otherwise known as 2-magnesium halo-3-pentene. The reaction with the magnesium is carried out preferably in the presence of tetrahydrofuran, however, other solvents such as diethyl ether may also be used. The mole ratio of magnesium to halo-pentene is preferably from 1 up to 10 moles of magnesium per mole of halo-pentene. More preferably, from 3 up to 5 moles of magnesium per mole of halo-pentene. The temperature of reaction is from 10° up to 50°C; preferably from 10° up to 20°C. Temperatures lower than 10°C gives rise to a reaction rate which is too slow to be economical. Temperatures higher than 50°C give rise to side reactions causing an undue lowering of yield of product;
  c. The Grignard reagent produced in step (b) is then reacted with carbon dioxide (preferably in the form of crushed dry ice). The reaction with carbon dioxide may also be carried out by bubbling carbon dioxide into the Grignard reagent at atmospheric pressure at a temperature of between −20° up to +40°C, preferably from 0° to 20°C or reacting the Grignard reagent with gaseous carbon dioxide at higher pressures of from 10 up to 100 pounds per square inch absolute at temperatures up to 50°C. When the reaction takes place with crushed dry ice, the temperature is the temperature of crushed dry ice. The carbonation forms magnesium halo salt of 2-methyl-3-pentenoic acid having the structure:

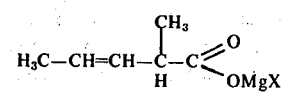

wherein X is halogen selected from the group consisting of chlorine and bromine;
  d. The last step in this process of the prior art involves the hydrolysis of the magnesium halo salt of 2-methyl-3-pentenoic acid in acid at a pH of from 2 up to 3. The preferred acid is a mineral acid such as hydrochloric acid or sulfuric acid.

A second process (which is novel) for producing another of the isomer mixtures containing a high proportion of cis-2-methyl-3-pentenoic acid, to wit approximately 80% cis-2-methyl-3-pentenoic acid and 20% 2-methyl-2-pentenoic acid involves the steps of:
  a. First preparing a methyl acetylene magnesium halide Grignard reagent by admixing, a methyl magnesium halide (the chloride, bromide or iodide) with a slight molar excess of methyl acetylene (preferably as "Mapp Gas", a commercial mixture of methyl acetylene and allene) at a temperature in the range of 40°–60°C (preferably 40°–50°C) in an inert solvent such as tetrahydrofuran or diethyl ether. Preferably, the reaction time range is from 4–12 hours;
  b. Preparing 3-pentyne-2-ol by first admixing the methyl magnesium halide reaction product preferably in its original reaction solvent with a slight molar excess of acetaldehyde to form a magnesium halo salt of 3-pentyne-2-ol, at a temperature in the range of 20°–30°C and then hydrolyzing the said magnesium halo salt of 3-pentyne-2-ol, preferably with a cold concentrated mineral acid such as concentrated hydrochloric acid in ice, and purifying the resulting 3-pentyne-2-ol using standard physical separation techniques, e.g., extraction and distillation;
  c. Preparing a 4-halo-2-pentyne (e.g., 4-chloro-2-pentyne or 4-bromo-2-pentyne) by means of halogenating the 3-pentyne-2-ol with a slight molar excess halogenating agent, e.g., phosphorous trichloride, phosphorous tribromide, and $SOCl_2$, at temperatures in the range of 20°–80°C, depending upon the halogenation reagent used. The preferred halogenating reagent is $PCl_3$ using a temperature range of 20°–25°C;
  d. Preparing a 4-magnesium-halo-2-pentyne Grignard reagent by reaction of the 4-halo-2-pentyne with magnesium in a solvent, for example, tetrahydrofuran or diethyl ether at a temperature in the range of 25°–50°C, depending upon the solvent used;

e. Preparing a magnesium halo carboxylate salt mixture of compounds having the structures:

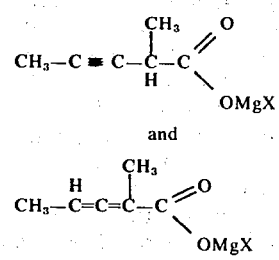

and (wherein X is halogen, e.g., chloro or bromo) by intimately admixing carbon dioxide (either in the gas phase, or as a solid in the form of powdered dry ice). The reaction with carbon dioxide may be carried out by bubbling carbon dioxide into the Grignard reagent at atmospheric pressure at a temperature of between −20° up to +40°C, preferably, from 0° to 20°C or reacting the Grignard reagent with gaseous carbon dioxide at higher pressures of from 10 up to 1000 pounds per square inch absolute at temperatures up to 50°C. When the reaction takes place with crushed dry ice, the temperature is the temperature of crushed dry ice.

f. Hydrolyzing the resulting magnesium halocarboxylate salt mixture with aqueous mineral acid (e.g., hydrochloric acid) at a temperature in the range of 20°–30°C to produce a crude mixture of:
 i. 2-methyl-3-pentynoic acid; and
 ii. 2-methyl-2,3-pentadienoic acid in a (i):(ii) ratio of 3:1;

g. Preparing a mixture containing about 80% cis-2-methyl-3-pentenoic acid and 20% 2-methyl-2-pentenoic acid by hydrogenating the mixed acid product of step (f) supra in the presence of a palladium/CaSO₄ catalyst containing 3% Pd preferably at a pressure in the range of 20–200 psig; preferably in a lower alkanol solvent such as methanol or ethanol at temperatures in the range of 20°–40°C, preferably 20°–25°C. The preferred weight percent range of catalyst is from 0.1 up to 1%. The resulting acid reaction product may then be purified using standard physical separation techniques, e.g., extraction and distillation.

When the 2-methyl-3-pentenoic acid isomer mixture of our invention is used as a food flavor adjuvant, the nature of the co-ingredients included with the said 2-methyl-3-pentenoic acid isomer mixture in formulating the product composition will also serve to alter the organoleptic characteristics of the ultimate foodstuff treated therewith. As used herein, in regard to flavors the term "alter" in its various forms means "supplying or imparting flavor character or note to otherwise bland, relatively tasteless substances or augmenting the existing flavor characteristic where a natural flavor is deficient in some regard or supplementing the existing flavor impression to modify its quality, character or taste". As used herein the term "foodstuff" includes both solids and liquids ingestible materials which usually do, but need not, have nutritional value. Thus, foodstuffs include soups, convenience foods, beverages, dairy products, candies, vegetables, cereals, soft drinks, snacks and the like.

Substances suitable for use herein as co-ingredients or flavoring adjuvants are well known in the art for such use being extensively described in the relevant literature. Apart from the requirement that any such material be "ingestibly" acceptable and thus non-toxic or otherwise non-deleterious nothing particularly critical resides in selection thereof. Accordingly, such materials which may in general be characterized as flavoring adjuvants or vehicles comprise broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2 and 3 tertiary-butyl-4-hydroxyanisole), butylated hydroxy toluene (2,6-di-tertiarybutyl-4-methyl phenol), propyl gallate and the like and sequestrants, e.g., citric acid.

Thickener compounds include carriers, binders, protective colloids, suspending agents, emulsifiers and the like, e.g., agaragar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches pectins, and emulsifiers, e.g., mono-and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono-and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, turmeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanal, crotonal, diacetyl, beta, beta-dimethyl-acrolein, n-hexanal, 2-hexenal, cis-3-hexenal, 2-heptanal, 4-(p-hydroxyphenyl)-2-butanone, alpha-ionone, beta-ionone, methyl-3-butanone, 2-pentanone, 2-pentenal and propanal; alcohols, such as 1-butanal, benzyl alcohol, 1-borneol, trans-2-buten-1-ol, ethanol, geraniol, 1-hexanal, 2-heptanol, trans-2-hexenol-1, cis-3-hexen-1-ol, 3-methyl-3-buten-1-ol, 1-pentenol, 1-penten-3-ol, p-hydroxyphenyl-2-ethanol, isoamyl alcohol, isofenchyl alcohol, phenyl-2-ethanol, alpha-terpineol, cis-terpineol hydrate; esters, such as butyl acetate, ethyl acetate, ethyl acetoacetate, ethyl benzoate, ethyl butyrate, ethyl caproate, ethyl cinnamate, ethyl crotonate, ethyl formate, ethyl isobutyrate, ethyl isovalerate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl capronate, methyl isobutyrate, alphamethylbutyrate, propyl acetate, amyl acetate, amyl butyrate, benzyl salicylate, dimethyl anthranilate, ethyl methylphenylglycidate, ethyl succinate, isobutyl cinnamate and terpenyl acetate; essential oils, such as jasmine absolute, rose absolute, orris absolute, lemon essential oil, bulgarian rose, yara yara, natural raspberry oil and vanilla; lactones; sulfides, e.g., methyl sulfide and other materials such as maltol, acetoin and acetals (e.g., 1,1-diethoxyethane, 1,1-dimethoxyethane and dimethoxymethane.

The specific flavoring adjuvant selected for use may be either solid or liquid depending upon the desired physical form of the ultimate product, i.e., foodstuff, whether simulated or natural, and should, in any event, be capable of providing an environment in which the high cis 2-methyl-3-pentenoic acid can be dispersed or admixed to provide a homogeneous medium. In addition, selection of one or more flavoring adjuvants, as well as the quantities thereof, will depend upon the precise organoleptic character desired in the finished product. Thus, in the case of flavoring compositions, ingredient selection will vary in accordance with the foodstuff to which the flavor and aroma are to be imparted. In contradistinction, in the preparation of solid products, e.g., simulated foodstuffs, ingredients capable of providing normally solid compositions should be selected such as various cellulose derivatives.

As will be appreciated by those skilled in the art, the amount of high cis-2-methyl-3-pentenoic acid employed in a particular instance can vary over a relatively wide range whereby to its desired organoleptic effects having reference to the nature of the product are achieved. All parts and percentages given herein are by weight unless otherwise specified. Thus, correspondingly greater amounts would be necessary in those instances wherein the ultimate food composition to be flavored is relatively bland to the taste, whereas relatively minor quantities may suffice for purposes of enhancing the composition merely deficient in natural flavor or aroma. Thus, the primary requirement is that the amount selected to be effective, i.e., sufficient to alter the organoleptic characteristics of the parent composition, whether foodstuff per se or flavoring composition. Thus, the use of insufficient quantities of high cis-2-methyl-3-pentenoic acid will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, it is found that quantities of high cis-2-methyl-3-pentenoic acid ranging from a small but effective amount, e.g., 0.01 parts per million up to about 50 parts per million by weight based on total composition are suitable. Concentrations in excess of the maximum quantity stated are not normally recommended since they fail to prove commensurate enhancement of organoleptic properties. In those instances wherein the high cis-2-methyl-3-pentenoic acid is added to the foodstuff as an integral component of a flavoring composition, it is of course essential that the total quantity of flavoring composition employed be sufficient to yield an effective high cis-2-methyl-3-pentenoic acid concentration in the foodstuff product.

Food flavoring compositions prepared in accordance with the present invention preferably contain the high cis-2-methyl-3-pentenoic acid in concentrations ranging from about 0.015 up to about 10% by weight based on the total weight of said flavoring composition.

The compositions described herein can be prepared according to conventional techniques well known as typified by cake batters and vegetable juices can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the high cis-2-methyl-3-pentenoic acid with for example gum arabic, gum tragacanth, carrageenan and the like, and thereafter spray-drying the resultant mixture whereby to obtain the particular solid product. Pre-prepared flavor mixes in powder form, e.g., a vanilla powder mix or a walnut flavored powder mix are obtained by mixing the dried solid components, e.g., starch, sugar, and the like and high cis-2-methyl-3-pentenoic acid in a dry blender until the requisite degree of uniformity is achieved.

It is presently preferred to combine with the 2-methyl-3-pentenoic acid isomer mixture the following adjuvants:

Geraniol
Ethyl methyl phenyl glycidate
Vanillin
Ethyl pelargonate
Isoamyl acetate
Ethyl butyrate
Naphthyl ethyl ether
Ethyl acetate
Isoamyl butyrate
2-Methyl-2-pentenoic acid
Elemecine (4-allyl-1,2,6-trimethoxy benzene)
Isoelemecine (4-propenyl-1,2,6-trimethoxy benzene)

The high cis-2-methyl-3-pentenoic acid can also be used to improve and augment the organoleptic properties of tobacco and tobacco products. Thus, the said high cis-2-methyl-3-pentenoic acid will impart a sweet, more natural rum character to tobacco when used at levels of from 100 parts per million up to 500 parts per million based on the dry weight of the tobacco. "Tobacco" as used herein includes natural tobaccos such as burley, turkish tobacco, Maryland tobacco, tobacco-like products such as reconstituted tobacco of homogenized tobacco and tobacco substitutes intended to replace natural tobacco such as various vegetable leaves, for example, lettuce, cabbage leaves and the like.

The high cis-2-methyl-3-pentenoic acid and an auxiliary perfume ingredient, including, for example, alcohols, aldehydes, nitriles, esters, cyclic esters and natural essential oils, may be admixed so that the combined odors of the individual components produce a pleasant and desired fragrance, particularly and preferably in strawberry fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, the individual components will contribute its particular olfactory characteristics, but the over-all effect of the perfume composition will be the sum of the effects of each of the ingredients. Thus, the high cis-2-methyl-3-pentenoic acid isomer mixture can be used to alter the aroma characteristics of a perfume composition, for example, by utilizing or moderating the olfactory reaction contributed by another ingredient in the composition.

The amount of high cis-2-methyl-3-pentenoic acid of our invention which will be effective in perfume compositions depends on many factors, including the other ingredients, their amounts and the effects which are desired. It has been found that perfume compositions containing as little as 0.3% of high cis-2-methyl-3-pentenoic acid or even less (e.g., 0.05%) can be used to impart a scent odor to soaps, cosmetics or other products. The amount employed can range up to 5% of the fragrance components and will depend on considerations of cost, nature of the end product, the effect desired on the finished product and the particular fragrance sought.

The high cis-2-methyl-3-pentenoic acid is useful in perfume compositions as an olfactory component in detergents and soaps, space odorants and deodorants, perfumes, colognes, toilet water, bath preparations, such as bath oils, and bath solids; hair preparations, such as lacquers, brilliantines, pomades and shampoo; cosmetic preparations, such as creams, deodorants, hand lotions, and sun screens; powders, such as talcs, dusting powders, face powders and the like. When used as an olfactory component of a perfumed article, as little as 100 parts per million of high cis-2-methyl-3-pentenoic acid will suffice to impart a sweet, green, sharp strawberry character which is one of the key odor characteristics of strawberry perfume formulations. Generally, no more than 0.8% of high cis-2-methyl-3-pentenoic acid based on the ultimate end product is required in the perfume composition.

In addition, the perfume composition or fragrance composition of our invention can contain a vehicle, or carrier for the high cis-2-methyl-3-pentenoic acid. The vehicle can be a liquid such as an alcohol, a non-toxic alcohol, a non-toxic glycol, or the like. The carrier can also be an absorbent solid, such as a gum (e.g., gum arabic) or components for encapsulating the composition (such as gelatin).

It will thus be apparent that high cis-2-methyl-3-pentenoic acid can be utilized to alter the sensory properties, particularly organoleptic properties, such as flavor and/or fragrance of a wide variety of consumable materials.

The following examples are given to illustrate embodiments of the invention as it is presently preferred to practice it. It will be understood that these examples are illustrative, and the invention is not to be considered as restricted thereto except as indicated in the appended claims.

EXAMPLE I

Preparation of an Approximately 60:40 Cis:trans Mixture 2-methyl-3pentenoic acid

A. PREPARATION OF 4-CHLORO-2-PENTENE

Into a 3 liter flask equipped with stirrer, thermometer, reflux condenser, subsurface addition tube and inlet and outlet bubblers and cooling bath, 1000 gms. (14.8 moles) of 97.7% pure piperylene is charged. The piperylene is cooled to 10°C and the reaction vessel is purged with dry nitrogen. While passing in hydrogen chloride, the reaction mass is stirred vigorously and the reaction mass temperature is maintained at 10°–15°C with external cooling. The hydrogen chloride is added over a period of 7 hours. The reaction mass is then purged with nitrogen at room temperature for a period of 10–20 minutes to remove any excess hydrogen chloride. The crude product may then be used further without purification for the preparation of the 2-methyl-3-pentenoic acid isomer mixture. The amount of crude product obtained is 1,435 gms.

B. PREPARATION OF 2-METHYL-3-PENTENOIC ACID ISOMER MIXTURE

Into a 12 liter reaction vessel equipped with stirrer, thermometer, reflux condenser, dropping funnel, two bubblers, heating mantle and cooling bath, thoroughly purged with nitrogen, the following materials are charged: Magnesium Turnings 600 gms. Tetrahydrofuran 3 liters The magnesium-tetrahydrofuran mixture is heated to 50°C at which time 70 ml of a solution (produced by admixing 750 gms of 4-chloro-2-pentene produced in step (A) with 2 liters of tetrahydrofuran) is added to the magnesium-tetrahydrofuran mixture in the 12-liter reaction vessel with stirring. The reaction mass temperature increased indicating the initiation of a Grignard reaction. With stirring, the remainder of the 4-chloro-2-pentene-tetrahydrofuran solution is added over a period of 5 hours. During the first 30 minutes of the addition, the reaction mass is slowly cooled to 25°–30°C and after that time the reaction mass is maintained at 25°–30°C throughout the remainder of the addition. The reaction mass is then stirred for 1 hour at 25°–30°C.

7.2 Kilograms of finely crushed dry ice is added into a 22 liter reaction flask equipped with an air driven motor stirrer, addition tube and an inlet and outlet bubblers. The Grignard reagent produced in the 12 liter reaction vessel is siphoned onto the dry ice in the 22 liter flask thus leaving the excess magnesium turnings in the 12 liter flask. A nitrogen stream is used to prevent premature reaction of carbon dioxide at the inlet tube. The dry ice-Grignard reagent mixture is then stirred slowly until the excess carbon dioxide has evaporated. The time of stirring is 8 hours. 2.5 Liters of water is then added to dissolve the magnesium salt and tetrahydrofuran is recovered by distillation at atmospheric pressure to pot temperature of 80°C. 1.25 Liters of toluene is then added to the reaction mass followed by 750 ml of concentrated hydrochloride acid over a period of 30 minutes maintaining the temperature of the reaction mass between 30°–40°C. The reaction mass is then stirred for another 30 minutes without further heating or cooling. The organic layer is removed and the aqueous layer is extracted with 1.25 liters of toluene after which time the two organic layers are combined. The organic solution is then stripped of solvent and the crude 2-methyl-3-pentenoic acid is rushed over to a pot temperature of 180°C at 2 mm Hg. using a 2 liter still with a 2 inch splash column. The rushed over 2-methyl-3-pentenoic acid is then fractionated at 3 mm Hg. pressure and a vapor temperature of 62°-63°C on a 1½ inch × 18 inch Goodloe packed column after adding 40 gms. of Primol and 1 gm of Ionol. NMR, IR and Raman spectral analyses indicate that the material produced is a 60:60 cis: trans mixture of isomers of 2-methyl-3-pentenoic acid (weight: 38 gms.).

NOTE: Signal at 3.50 ppm attributed to "cis" isomer, and 3.10 ppm attributed to "trans" isomer.

EXAMPLE II

The following concentrate is prepared:

| Ingredient | Percent |
| --- | --- |
| Geraniol | 1.00 |
| Ethyl methyl phenyl glycidate | 3.33 |
| High cis-2-methyl-3-pentenoic acid (prepared according to the process of Example I) | 4.77 |
| Vanillin | 5.66 |
| Ethyl pelargonate | 13.06 |
| Isoamyl acetate | 14.00 |
| Ethyl butyrate | 58.18 |

EXAMPLE III

Another concentrate is prepared as follows:

| Ingredient | Percent |
| --- | --- |
| Naphthyl ethyl ether | 0.96 |
| Vanillin | 2.66 |
| Ethyl methyl phenyl glycidate | 2.88 |
| High cis-2-methyl-3-pentenoic acid (prepared according to the process of Example I) | 4.90 |
| Ethyl acetate | 9.58 |
| Isoamyl acetate | 12.25 |
| Ethyl butyrate | 26.20 |
| Isoamyl butyrate | 40.57 |

EXAMPLE IV

The concentrate prepared in Example II is dissolved in 4 volumes of propylene glycol and the mixture is added to a hard candy melt at the rate of 1.5 oz of the concentrate solution per 100 lbs. of melt. After the finished candy has been produced, it is found to have an excellent strawberry flavor. When the candy is compared with candy made under the same conditions, but without the 2-methyl-3-pentenoic acid prepared according to the process of Example I in the concentrate, it is found to have an inferior strawberry flavor.

EXAMPLE V

The propylene glycol solution of the concentrate as prepared in Example IV is added to a simple syrup at the rate of one-eighth oz. per gallon of syrup. The syrup is acidified by the addition of 1.5 oz. of 50% aqueous citric acid solution to each gallon of syrup. A carbonated beverage is prepared by admixing one oz. of the flavored, acidified syrup with 5 oz. of carbonated water. The beverage so prepared has an excellent fresh strawberry flavor, and is found to be markedly superior to a beverage prepared in the same manner but without the high cis-2-methyl-3-pentenoic acid prepared according to the process of Example I.

EXAMPLE VI

The flavor concentrate prepared in Example III is admixed with gum arabic and in the proportion of 7 lbs. of concentrate to 28 lbs. of gum arabic in 65 lbs. of water, and the aqueous mixture is spray-dried. The flavor concentrate-carrier combination so obtained is then added to a gelatin dessert mix in the ratio of 1 oz. of spray-dried material to 100 lbs. of dessert mix powder. The gelatin dessert produced from the mix has an excellent strawberry flavor and is markedly superior to a gelatin dessert prepared in the same manner without the 2-methyl-3-pentenoic acid prepared according to the process of Example I in the concentrate.

EXAMPLE VII

Strawberry Fragrance

The following mixture is prepared:

| Ingredient | Parts by Weight |
| --- | --- |
| Ethyl aceto acetate | 3 |
| Ethyl laurate | 10 |
| Cinnamyl isobutyrate | 3 |
| Cinnamyl isovalerate | 5 |
| Diacetyl | 2 |
| Heliotropyl acetate | 20 |
| Peach aldehyde coeur | 100 |
| Ethyl butyrate | 200 |
| Ethyl isovalerate | 20 |
| Ethyl heptoate | 1 |
| Dulcinyl | 5 |
| para-Hydroxy phenyl butanone | 2 |
| Ethyl acetate | 1 |
| Beta Ionone | 10 |
| Palatone | 2 |
| Ethyl vanillin | 1 |
| Hexadecanal | 150 |
| High cis-2-methyl-3-pentenoic acid (prepared according to the process of Example I) | 5 |

The high cis-2-methyl-3-pentenoic acid prepared according to the process of Example I imparts a definite green, sweet, sharp strawberry note to this strawberry fragrance.

EXAMPLE VIII

Tobacco Formulation

A tobacco mixture is produced by admixing the following materials:

| Ingredient | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredient | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above-stated tobacco flavor formulation is applied at the rate of 0.5% to all of the cigarettes produced using the above tobacco formulation. Half of the cigarettes are then treated with 5 and 10 ppm of 2-methyl-3-pentenoic acid produced according to the process of Example I. The control cigarettes not containing the 2-methyl-3-pentenoic acid produced according to the process of Example I and the experimental cigarettes which contain the 2-methyl-3-pentenoic acid produced according to the process of Example I are evaluated by paired comparison and the results are as follows:

The experimental cigarettes are found to be, on smoking, more aromatic, and richer in aroma, i.e., having a well pronounced, pleasant, full aroma.

In the smoke, the experimental cigarettes are found to be more aromatic, sweeter, more bitter, less harsh in the mouth and throat and slightly woody and smokey. All cigarettes are evaluated for smoke flavor with a 20 mm cellulose acetate filter.

The high cis-2-methyl-3-pentenoic acid produced according to the process of Example I enhances the tobacco-like taste and aroma of the blended cigarette and gives the cigarette a turkish-like character.

EXAMPLE IX

Preparation of Soap Composition

One hundred grams of soap chips are mixed with one gram of the perfume composition of Example VII until a substantially homogeneous composition is obtained. The perfumed soap composition manifests an excellent strawberry character with a green, sweet nuance.

EXAMPLE X

Preparation of a Detergent Composition

A total of 100 g of a detergent powder is mixed with 0.15 g of the perfume composition of Example VII until a substantially homogeneous composition is obtained. This composition has an excellent strawberry fragrance.

EXAMPLE XI

Preparation of a Cosmetic Powder Composition

A cosmetic powder is prepared by mixing in a ball mill, 100 g of talcum powder with 0.25 g of 2-methyl-3-pentenoic acid 3:2 cis:trans isomer mixture prepared according to Example I. It has an excellent sweet, green, strawberry aroma.

EXAMPLE XII

Perfumed Liquid Detergent

Concentrated liquid detergents with a fruity, chamomile odor are prepared containing 0.10%, 0.15% and 0.20% of high cis-2-methyl-3-pentenoic acid prepared according to Example I. They are prepared by adding and homogeneously mixing the appropriate quantity of high cis-2-methyl-3-pentenoic acid in the liquid detergent. The detergents all possess a sweet, green strawberry fragrances, the intensity increasing with greater concentration of high cis-2-methyl-3-pentenoic acid.

EXAMPLE XIII

Preparation of a Cologne and Handkerchief Perfume

High cis-2-methyl-3-pentenoic acid prepared according to the process of Example I is incorporated in a cologne at a concentration of 2.5% in 85% aqueous ethanol; and into a handkerchief perfume at a concentration of 20% (in 95% aqueous ethanol). A distinct and definite sweet, green, strawberry fragrance is imparted to the cologne and to the handkerchief perfume.

EXAMPLE XIV

Preparation of a Cologne and Handkerchief Perfume

The composition of Example VII is incorporated in a cologne at a concentration of 2.5% in 85% aqueous ethanol; and into a handkerchief perfume at a concentration of 20% (in 95% aqueous ethanol). The use of the high cis-2-methyl-3-pentenoic acid in the composition of Example VII affords a distinct and definite strong strawberry aroma with a sweet, green note to the handkerchief perfume and cologne.

EXAMPLE XV

Preparation of Soap Composition

One hundred grams of soap chips are mixed with one gram of 3:2 cis:trans 2-methyl-3-pentenoic acid until a substantially homogeneous composition is obtained. The perfumed soap composition manifests an excellent strawberry aroma with a sweet, green note.

EXAMPLE XVI

Preparation of a Detergent Composition

A total of 100 g of a detergent powder is mixed with 0.15 g of the isomer mixture of 3:2 cis:trans-2-methyl-3-pentenoic acid of Example I until a substantially homogeneous composition is obtained. This composition has an excellent strawberry aroma with a sweet, green note.

EXAMPLE XVII

Preparation of a Cosmetic Powder Composition

A cosmetic powder is prepared by mixing in a ball mill 100 g of talcum powder with 0.25 g of 2-methyl-3-pentenoic acid 3:2 cis:trans isomer mixture prepared according to Example I. It has an excellent sweet, green, strawberry character.

EXAMPLE XVIII

Preparation of Mixture Containing 80% Cis-2-methyl-3-pentenoic Acid and 20% 2-Methyl-2-pentenoic acid A. PREPARATION OF 3-pentyn-2-OL
Equipment: 5 liter reaction flask Material:

| | |
|---|---|
| Methyl magnesium chloride (3 molar in tetrahydrofuran) | 3 liters |
| Mapp gas (Mixture of methyl acetylene and allene) | 600 g |
| Acetaldehyde (6 molar) | 264 g |

Procedure: Mapp gas is passed through a sodium hydroxide drying tube into the methyl magnesium chloride solution at 40°–50°C. The operation takes 5 hours to completion. The mixture is heated to 50°C for an additional 2 hours before cooling. To the cold solution is added 264 g of acetaldehyde at 20°–30°C over 2 hours with cooling. The mixture is then stirred for 1 hour at 25°C and is then decomposed with 800 ml of concentrated hydrochloric acid and 5 kg of ice. The resulting lower layer is extracted with one liter of benzene. The combined organic liquids are washed with two 200 ml portions of 20% aqueous NaCl and distilled at atmospheric pressure to a pot temperature of 92°C and then rushed over under vacuum. The rushed over material is then topped at 45–50 mm Hg. pressure to a pot temperature of 72°C (weight of product: 92 grams). After the topping, this material is used to prepare 4-chloro-2-pentyne in part B, infra, without further purification.

B. PREPARATION OF 4-CHLORO-2-pentyne

Equipment: 250 ml reaction flask
Material:

| | |
|---|---|
| 3-Pentyn-2-ol | 84 g (Ex part A) |
| Phosphorous trichloride | 69 g |

Procedure: The phosphorus trichloride is added at 20°–25°C with cooling to the 3-pentyn-2-ol prepared in part A, supra. The mixture is stirred for 12 hours at 20°–25°C and then heated to 72°C for 5 hours. IR analysis indicates that the reaction is complete. The material is then rushed over under vacuum to give 4-chloro-2-pentyne for the Grignard reaction exemplified in part C, infra. The yield is nearly quantitative.

C. PREPARATION OF 2-METHYL-3-PENTYNOIC ACID

Equipment: 1 liter reaction flask
Material:

| | |
|---|---|
| 4-Chloro-2-pentyne | 46 g |
| Magnesium chips | 60 g |
| Tetrahydrofuran (dry) | 500 ml |

Procedure: 4-Chloro-2-pentyne is dissolved in 200 ml of tetrahydrofuran and added over 4½ hours (after starting the reaction with iodine crystals) to the magnesium chips in 300 ml of tetrahydrofuran. The reaction temperature rises to 44°–50°C in the initiation period and is maintained at 28°–30°C with external cooling. The reaction mixture is allowed to stir for an additional hour after all of the 4-chloro-2-pentyne is added. The resulting Grignard reagent is poured onto 620 g of dry ice (powdered) with stirring. After the $CO_2$ evaporates, 300 ml of water is added and the solution is extracted with three 200 ml portions of toluene. The toluene extracts are discarded. The aqueous solution is cooled and acidified with 50 ml of concentrated hydrochloric acid; then extracted with two 200 ml portions of toluene. The toluene extract, after washing with three 50 ml portions of 20% NaCl solution is stripped of solvent and rushed over to give 22 g of crude acids. The crude product is then fractionated in a semi-micro still to give 6.2 g of an acid mixture which contains a 3:1 mixture of 2-methyl-3-pentynoic acid and 2-methyl-2,3-pentadienoic acid.

D. HYDROGENATION REACTION

Equipment: Parr Shaker
Material:

| | |
|---|---|
| Mixture of 2-methyl-3-pentynoic acid and 2-methyl-2,3-pentadienoic acid | 4 g |
| Methanol (absolute) | 50 ml |
| 3% Pd/CaSO$_4$ | 0.1 g |

Procedure: The 2-methyl-3-pentynoic acid and 2-methyl-2,3-pentadienoic acid mixture produced in part C, supra, is hydrogenated at room temperature in methanol in the presence of Pd/CaSO$_4$ catalyst at a hydrogen pressure of 44.5 psig. The reaction is complete in 5 minutes. After removal of the methanol, the residue oil is analyzed by GLC which shows one peak. However, NMR analysis shows two products confirmed to be cis-2-methyl-3-pentenoic acid and 2-methyl-2-pentenoic acid. (A 4:1 mixture).

EXAMPLE XIX

Flavor Formulation Containing Mixture of 80% Cis-ethyl-2-methyl-3-pentenoate and 20% Ethyl-2-methyl-2-pentenoate The following basic strawberry formulation is prepared:

| Ingredient | Parts by Weight |
|---|---|
| Parahydroxy benzyl acetone | 0.2 |
| Vanillin | 1.5 |
| Maltol | 2.0 |
| Ethyl-3-methyl-3-phenyl glycidate | 1.5 |
| Benzyl acetate | 2.0 |
| Ethyl butyrate | 1.0 |
| Methyl cinnamate | 0.5 |
| Methyl anthranilate | 0.5 |
| Alpha-ionone | 0.1 |
| Gamma undecalactone | 0.2 |
| Diacetyl | 0.2 |
| Anethole | 0.1 |
| Cis-3-hexenol | 1.7 |
| 95% aqueous ethanol | 38.5 |
| Propylene glycol | 50.0 |
| | 100.0 |

To a portion of the foregoing formulation, 0.2% by weight of a mixture of 80% cis-2-methyl-3-pentenoic acid and 20% 2-methyl-2-pentenoic acid prepared according to the process of Example XVIII is added. The formulation with the high cis-2-methyl-3-pentenoic acid is compared to the same formulation without said high cis-2-methyl-3-pentenoic acid.

Both flavors are evaluated in a milk beverage sweetened with 10% sugar at the rate of 100 ppm. Both beverages are tasted by an expert panel. The beverage containing the strawberry formulation with the addition of the mixture containing 80% cis-2-methyl-3-pentenoic acid is unanimously preferred as having a more natural like, strawberry aroma, a sweeter, more green, more pleasant strawberry taste and a sweet, strawberry after-taste.

EXAMPLE XX

Tobacco Flavor Formulation and Tobacco

A tobacco mixture is produced by admixing the following materials:

| Ingredient | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredient | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol (95% aqueous) | 20.00 |
| Water | 41.90 |

The above-stated tobacco flavor formulation is applied at the rate of 0.1% to all of the cigarettes produced using the above tobacco formulation. Half of the cigarettes are then treated with 100 or 200 ppm of the mixture containing 805 cis-2-methyl-3-pentenoic acid and 20% ethyl-2-methyl-2-pentenoic acid produced according to the process of Example XVIII.

The control cigarettes not containing the mixture having 80% cis-2-methyl-3-pentenoic acid produced according to the process of Example XVIII and the experimental cigarettes which do contain the mixture having 80% cis-2-methyl-3-pentenoic acid produced according to the process of Example XVIII are evaluated by paired comparison, and the results are as follows:

In aroma, the cigarettes containing the mixture having 80% cis-2-methyl-3-pentenoic acid have been found to be more aromatic.

In smoke flavor, the cigarettes containing the mixture having 80% cis-2-methyl-3-pentenoic acid are more aromatic, more sweet, more bitter, slightly less harsh in the mouth and throat and leave a slight, sweet chemical mouth-coating effect similar to Turkish tobacco.

In summary, the mixture having 80% cis-2-methyl-3-pentenoic acid enhances the tobacco-like taste and aroma of a blended cigarette and imparts to that cigarette a Turkish-like character in smoke flavor.

EXAMPLE XXI

Strawberry Fragrance

The following mixture is prepared:

| Ingredient | Parts by Weight |
| --- | --- |
| Ethyl acetoacetate | 3 |
| Ethyl laurate | 10 |
| Cinnamyl isobutyrate | 3 |
| Cinnamyl isovalerate | 5 |
| Diacetyl | 2 |
| Heliotropyl acetate | 20 |
| Peach aldehyde coeur | 100 |
| Ethyl butyrate | 200 |
| Ethyl isovalerate | 20 |
| Ethyl heptanoate | 1 |
| Dulcinyl | 5 |
| 2(para-hydroxyphenyl)-3-butanone | 2 |
| Ethyl acetate | 1 |
| Beta-ionone | 10 |
| Palatone | 2 |
| Ethyl vanillin | 1 |
| Ethyl-3-methyl-3-phenyl glycidate | 150 |
| Mixture containing 80% cis-2-methyl-3-pentenoic acid (prepared according to the process of Example XVIII) | 5 |

The mixture containing 80% cis-2-methyl-3-pentenoic acid prepared according to the process of Example XVIII imparts a green, sweet, fresh strawberry note to this strawberry fragrance.

EXAMPLE XXII

Preparation of Soap Composition

One hundred grams of soap chips are mixed with one gram of the perfume composition of Example XXI until a substantially homogeneous composition is obtained. The perfumed soap composition manifests an excellent strawberry character with a sweet, green nuance.

EXAMPLE XXIII

Preparation of a Detergent Composition

A total of 100 g of a detergent powder is mixed with 0.15 g of the perfume composition of Example XXI until a substantially homogeneous composition is obtained. This composition has an excellent strawberry fragrance.

EXAMPLE XXIV

Preparation of a Cosmetic Powder Composition

A cosmetic powder is prepared by mixing in a ball mill 100 g of talcum powder with 0.25 g of the mixture containing 80% cis-2-methyl-3-pentenoic acid prepared according to Example XVIII. It has an excellent sweet, green, strawberry aroma.

EXAMPLE XXV

Perfumed Liquid Detergent

Concentrated liquid detergents with a fruity, chamomile odor are prepared containing 0.10%, 0.15% and 0.20% of the mixture having 80% cis-2-methyl-3-pentenoic acid prepared according to Example XVIII. They are prepared by adding and homogeneously mixing the appropriate quantity of mixture containing 80% cis-2-methyl-3-pentenoic acid in the liquid detergent. The detergents all possess a sweet, green, strawberry fragrance, the intensity increasing with greater concentrations of mixing containing 80% cis-2-methyl-3-pentenoic acid.

EXAMPLE XXVI

Preparation of a Cologne and Handkerchief Perfume

The composition of Example XXI is incorporated in a cologne at a concentration of 2.5% in 85% aqueos ethanol; and into a handkerchief perfume at a concentration of 20% (in 95% aqueous ethanol). The use of the mixture containing 80% cis-2-methyl-3-pentenoic acid in the composition of Example XXI affords a distinct and definite strong strawberry aroma with a sweet, green note to the handkerchief perfume and cologne.

EXAMPLE XXVII

Preparation of Soap Composition

One hundred grams of soap chips are mixed with one gram of mixture containing 80% cis-2-methyl-3-pentenoic acid of Example XVIII until a substantially homogeneous composition is obtained. The perfumed soap composition manifests an excellent strawberry aroma with a sweet, green note.

EXAMPLE XXVIII

Preparation of a Detergent Composition

A total of 100 g of a detergent powder is mixed with 0.15 g of the mixture containing 80% cis-2-methyl-3-pentenoic acid of Example XVIII until a substantially homogeneous composition is obtained. This composition has an excellent strawberry aroma with a sweet, green note.

What is claimed is:

1. A process for preparing a mixture containing 80% cis-2-methyl-3-pentenoic acid and 20% 2-methyl-2-pentenoic acid comprising the steps of:
   a. reacting in the presence of a non-reactive solvent at a temperature in the range of 40°–60°C methyl acetylene with a methyl magnesium halide to form a methyl acetylene magnesium halide Grignard reagent;
   b. reacting in the presence of a non-reactive solvent at a temperature in the range of 20°–30°C the methyl acetylene magnesium halide Grignard reagent with acetaldehyde to form a 3-pentyn-2-ol magnesium halide salt;
   c. hydrolyzing said 3-pentyn-2-ol magnesium halide salt with concentrated mineral acid to form 3-pentyn-2-ol;
   d. reacting in the presence of a non-reactive solvent at a temperature in the range of 20°–30°C the methyl acetylene magnesium halide Grignard reagent with acetaldehyde to form a 3-pentyn-2-ol magnesium halide salt;
   e. reacting in the presence of a non-reactive solvent at a temperature in the range of 25°–50°C said 4-halo-2-pentyne with magnesium to form a 4-magnesium halo-2-pentyne Grignard reagent;
   f. reacting said 4-magnesium halo-2-pentyne Grignard reagent with $CO_2$ to form a magnesium halo carboxylate salt mixture;
   g. hydrolyzing said magnesium halo carboxylate salt mixture with aqueous mineral acid at a temperature in the range of 20°–30°C to form a mixture of 2-methyl-3-pentenoic acid and 2-methyl-2,3-pentadienoic acid; and
   h. reacting in the presence of a non-reactive solvent said mixture of 2-methyl-3-pentynoic acid and 2-methyl-2,3-pentadienoic acid with hydrogen; the reaction taking place at a pressure of 20°–200 psig and a temperature in the range of 20°–40°C in the presence of a $Pd/CaSO_4$ catalyst to form a mixture containing 80% cis-2-methyl-3-pentenoic acid and 20% 2-methyl-2-pentenoic acid.

* * * * *